(12) United States Patent
Joyce

(10) Patent No.: US 11,497,837 B2
(45) Date of Patent: Nov. 15, 2022

(54) MOLDED PARTS WITH THERMOPLASTIC CELLULOSE BIOPOLYMER COMPOSITIONS HAVING ORIENTED FIBERS FOR MEDICAL DEVICES AND IMPLANTS

(71) Applicant: Innovative Plastics and Molding, Inc., Toledo, OH (US)

(72) Inventor: Robert Curt Joyce, Toledo, OH (US)

(73) Assignee: Innovative Plastics and Molding, Inc., Toledo, OH (US)

( * ) Notice: Subject to any disclaimer, the term of this patent is extended or adjusted under 35 U.S.C. 154(b) by 366 days.

(21) Appl. No.: 15/330,961

(22) Filed: Jan. 11, 2016

(65) Prior Publication Data

US 2017/0296707 A1 Oct. 19, 2017

Related U.S. Application Data

(60) Provisional application No. 62/125,113, filed on Jan. 14, 2015.

(51) Int. Cl.
| | |
|---|---|
| *A61L 31/06* | (2006.01) |
| *C08L 77/00* | (2006.01) |
| *C08L 23/02* | (2006.01) |
| *A61L 31/04* | (2006.01) |
| *A61L 31/14* | (2006.01) |
| *A61L 31/12* | (2006.01) |
| *A61L 27/56* | (2006.01) |
| *C08L 23/12* | (2006.01) |
| *A61L 27/48* | (2006.01) |

(52) U.S. Cl.
CPC .............. *A61L 31/06* (2013.01); *A61L 27/48* (2013.01); *A61L 27/56* (2013.01); *A61L 31/042* (2013.01); *A61L 31/048* (2013.01); *A61L 31/129* (2013.01); *A61L 31/146* (2013.01); *C08L 23/02* (2013.01); *C08L 23/12* (2013.01); *C08L 77/00* (2013.01)

(58) Field of Classification Search
CPC .......... A61L 31/06; A61L 27/48; A61L 27/56; A61L 31/042; A61L 31/048; A61L 31/129
See application file for complete search history.

(56) References Cited

U.S. PATENT DOCUMENTS

| 4,810,570 A * | 3/1989 | Rutten | C08J 9/06 264/45.5 |
| 6,562,447 B2 * | 5/2003 | Wu | B29C 47/0816 428/305.5 |
| 7,083,849 B1 * | 8/2006 | Albrecht | B29C 44/5627 427/208 |
| 8,463,418 B2 * | 6/2013 | Liu | B29C 48/266 700/119 |
| 2003/0008127 A1 * | 1/2003 | Stimler | B29C 44/22 428/304.4 |
| 2003/0077311 A1 * | 4/2003 | Vyakarnam | A61L 31/06 424/426 |
| 2004/0126558 A1 * | 7/2004 | Williams | B32B 5/18 428/304.4 |
| 2008/0190924 A1 * | 8/2008 | Bobrov | B29C 44/0407 220/62.22 |
| 2011/0245380 A1 * | 10/2011 | Joyce | C08L 97/02 524/13 |
| 2017/0067207 A1 * | 3/2017 | Malkki | A61L 15/28 |
| 2018/0258259 A1 * | 9/2018 | Banerjie | C08L 101/00 |
| 2019/0111175 A1 * | 4/2019 | Luukko | A61L 15/44 |

OTHER PUBLICATIONS

"Review on the Additive Manufacturing of Fiber Reinforced Polymer Matrix Composites" Evren Yasa, Kivilcim Ersoy; Solid Freeform Fabrication 2018: Proceedings of the 29th Annual INternational Solid Freeform fabrication Symposium—An additive manufacturing Conference (2018).*

A Le Duigou: "3D printing of wood fibre biocomposites: from mechanical to actuation functionality" Materials and Design 96 (2016) 106-114.*

Balla: Vamsi Krishna "Additive manufacturing of natural fiber reinforced polymer composites: processing and prospects" Composites Part B 1174 (2019) 106956.*

"Nanocellulose in polymer composites and biomedical applications" Yuan Lu, Halil Levent Tekinalp, Claude Clifford Eberle, William Peter, Amit Kumar Naskar, and Soydan Ozcan; Tappi Journal Jun. 2014 (vol. 12, No. 6) (Year: 2014).*

\* cited by examiner

*Primary Examiner* — Kevin R Kruer

(74) *Attorney, Agent, or Firm* — MacMillan, Sobanski & Todd, LLC

(57) ABSTRACT

A longitudinal extending body with oriented fibers comprised of an organic compound, preferably cellulose fibers, with a hydrophilic and hydrophobic polymer having absorbable and non res sorbable qualities in the body, with an internal construction to promote cell growth. The longitudinal body has at least one wall having oriented fiber to include cellulose fiber extending the length of said body. This extending body has a surface that is smooth to the touch for additional processing methods such as machining, compression molding and 3 D printing.

15 Claims, No Drawings

MOLDED PARTS WITH THERMOPLASTIC CELLULOSE BIOPOLYMER COMPOSITIONS HAVING ORIENTED FIBERS FOR MEDICAL DEVICES AND IMPLANTS

CROSS REFERENCES

Application claims priority of U.S. Provisional Patent Application Ser. No. 62/125,113 filed Jan. 14, 2015, this prior application are incorporated herein by reference.

FIELD OF INVENTION

The present invention relates to a molded parts and, more particularly, to a longitudinal body that can be produced by an orientation method. This longitudinal body is molded for medical related products such as devices and implants that require approval of non toxicity and specific performance testing. In a preferred embodiment, molded parts comprising of two ingredients, an organic compound, most desirable, a cellulose fiber having oriented fibers, two dissimilar thermoplastics and a coupling that are compounded to produce a plastic alloy composition with considerable improvement in flexural strength. This thermoplastic cellulose fiber composition with oriented fibers will have a high degree of compressive strength, absorbable qualities with two hydrophilic components. In this invention, a compound comprising of an organic compound preferably cellulose fiber, a polyolefin, which is hydrophobic and a hydrophilic polymer, most preferably polyamide is processed to help achieve a biocompatible composition with an orientation method for cellulose fiber alignment to replace a less pure and more expensive polymer like medical polyetheretherketone (PEEK). Furthermore, this invention will have porosity or sometimes referred to as a cellular structure within to promote tissue, cell growth and is not re sorbable by the body, which is novel for implantable devices.

BACKGROUND OF INVENTION

In the medical field, material technology is an area that is constantly being scrutinized because of the costs and performance. The materials presently being used in medical products, to include devices and implants, are ceramics, thermoplastics, biomaterials and metals. Some of these high strength materials have lacked attributes such as absorbable qualities, along with a compressive strength to obtain the desired torque and axial loads. In some of the present technology like metals, certain devices and implants have shown to cause toxicity in the human body due to lack of biocompatibility. Furthermore, some of the materials will lack in functionality like elasticity and have poor sterilization qualities. Metal based implants cause inflammation and swelling due to metal ion migration and accumulation on tissue (Healy & Ducheyne,1991). On the other hand, commercially used polymer based materials such as carbon coated polymers and polyetheretherketones PEEK cause strong cellular absorption, also resulting in high levels of inflammation (Milhov & Katerska, 2010; Kasemo, 2004) The primary reason for bio-incompatibility is a hydrophobic environment at the cell-material interface. Another recurring problem with the polymeric implant materials, from a commercial standpoint, is the mechanical load bearing capacity (Nag & Banerjee, 2012) Because of the shortcoming in mechanical strength, currently existing implant materials fail to acquire significant durability, resulting in more frequent surgeries and less cost-effectiveness. The existing high strength thermoplastic materials for medical devices and implants, like medical PEEK, are not purified without extensive processing in a compounding operation or a need to be sterilized. For instance, medical PEEK is a very high energy intensive thermoplastic resin that requires multiple processing methods for purification before being extruded to make two dimensional shapes like bar stock, rods, and sheets. Furthermore, a secondary, and possibly a third process might be necessary to help the manufacture produce parts for medical devices, implants and instruments. An additional process like machining, 3 D printing, compression and or injection molding can help make a three dimensional shape.

One of these materials for medical devices and implants, medical PEEK has a strength in the 14,000 psi range, with the ability to support the desired property requirements for medical device/bone replacement determined by the medical community. The medical polyetheretherketone (PEEK) is expensive, requires multiple processing levels, computerized machining techniques and coatings to be utilized in the body for spinal cages, screws, etc. The current medical PEEK does not demonstrate porosity to encourage cell growth within the composition had is considered too brittle or lacking elasticity for some applications. This creates difficulty for the surgeon and patient as it relates to healing process for the body to attach certain ligaments, tissue, etc. to help support the implantable device or implant. These limitations with medical PEEK will also sometimes prohibit patients from selection of a possible solution for medical device or bone replacement.

Typical applications of biomaterials in medicine are for disposable products (e.g. syringe, blood bag, and cathe-ter), materials supporting surgical operation (e.g. suture, adhesive, and sealant), prostheses for tissue replacements (e.g. intraocular lens, dental implant, and breast implant), and artificial organs for temporary or permanent assist (e.g. artificial kidney, artificial heart, and vascular graft). The biomaterials having re sorbable qualities have made significant advances in implantable medical devices and implants. These re sorbable biomaterials have hygroscopic tendencies. The non re sorbable biomaterials with absorbable fibers like microbial fibers have been elusive especially without hygroscopic qualities. Furthermore, these biomaterials are a new material technology with exposure to the human body or biocompatibility, which constitutes heavy governmental regulations for approval include non-toxicity, sterilizability, and effectiveness. A large unsolved problem of biomaterials is this lack of biocompatibility, especially when they are used not temporarily but permanently as implants in our body. Biocompatibility is highly desirable but not indispensable; most of the clinically used biomaterials lack excellent biocompatibility, although many efforts have been devoted to the development of biocompatible materials by biomaterials scientists and engineers.

The existing cellulose from wood pulp has typical chain lengths between 300 and 1700 units; cotton and other plant fibers as well as bacterial cellulose have chain lengths ranging from 800 to 10,000 units. Plant-derived cellulose is usually found in a mixture with hemicellulose, lignin, pectin and other substances, while bacterial cellulose is quite pure, has a much higher water content and higher tensile strength due to higher chain lengths. This thermoplastic cellulose biopolymer compositions requires the orientation of cellulose fibers due to low strength and or performance constraints like elasticity and impact. This biopolymer composition will include cellulose fiber from chain lengths primarily between 300 and 1700 units that is conducive to process with thermoplastic polyolefin and polyamide. The orientation of these cellulose fibers in the thermoplastic matrix will produce medical devices and products having better function like elasticity, strength performance, compressibility at a lower specific gravity to help reduce medical costs and improve performance.

DESCRIPTION OF RELATED ART

For many years, surgeons, orthotists and patients have had to work with crude shapes and modifications of materials. The choices for materials in medical devices and implantable's are limited. Primarily metals, thermoplastics, bio materials and in some forms, coated and non coated cellulose. The metals like titanium are for load bearing structural applications. Thermoplastics and bio materials are being developed to create new and improved products but still have limitations with strength and elasticity. The metals, thermoplastics have little if any biocompatibility without a secondary treatment. In some cases, cellulose has been used in various non structural forms to offer relief. It is critical for the ingredients of a composition to have some history of exposure or bio compatibility to the body to produce a medical device or implant.

Polypropylene is used in approximately 77% of all injection molded medical devices. The nature of the polypropylene is hydrophobic and will repel the water molecules forming ionic or a hydrogen bond with the water molecule. This property of water was important for the evolution of life. Hydrophobic interaction plays the most critical roles in the formation of the lipid bilayer of the cell membrane and the folding of proteins and nucleic acids; therefore, hydrophobic, interaction is the foundation for the existence of life. The applications for the hydrophobic polypropylene in the medical implants include hernia repair meshes and sutures. Polypropylene has limitations in performance strength—3,000 to 4,000 psi. and creep, making this thermoplastic un acceptable for long term vascular implants. The effect of radiation is also of concern with polypropylene where color are effected without stabilizers and elongation decreases and embrittlement increases to unacceptable levels for medical devices. Furthermore, polypropylene has a narrow processing window and warpage is common which prohibits the polymer from use in some medical applications that are 3 D printed. The medical devices and implants are being 3 D printed because of the necessary customization of medical devices and implants. For 3 D printing, other plastics like silicon, are frequently used, however, this material has it's challenges with strength, adhesion and structural applications. In general terms, it has been difficult for most thermoplastics like polypropylene to participate in medical devices and implants because of various performance issues like processing capabilities and performance capabilities.

The high strength materials for implants like medical PEEK, without any reinforcements like carbon fiber, has a tensile strength of 15,000 psi. Medical PEEK with reinforcements like carbon fiber have been shown to reach beyond the tensile strength of 20,000 psi., The medical PEEK is somewhat versatile with the ability to apply coatings for implants to promote cell growth. The medical PEEK can be used for structural and non structural bone implants and has an approximate density of 1.3 g/cc, which is very high compared to bone. Medical PEEK is primarily extruded, then computer numerically machined to a specific shape and then most likely sterilized before insertion into the body. Furthermore, the entire process for preparing medical PEEK for bone replacement is lengthy and very expensive. There has been a difficult challenge for medical PEEK to promote cell growth outside the molded part and or machined part without coatings. The author has not seen any evidence of in vitro cell growth within a medical PEEK part or internal cell growth for any identified biopolymer resin that has the necessary strength for implants. Furthermore, good flexibility or elasticity is required for a bone replacement. These high strength thermoplastic materials like medical PEEK have limited elasticity and will break if loads are exceeded.

Bone can be defined as a structure composed of hydroxyapatite crystals deposited within an organic matrix (of which ~95% is collagen). It is composed of 'trabecular' (spongy) bone, which creates a porous environment with 50-90% porosity (the fraction of empty space in a volume) and pore sizes around 1 mm in diameter, with 'cortical' (compact) bone surrounding it. To induce the growth of normal bone tissue, we ideally want biomaterial scaffolds with a high surface area for cell attachment and tissue ingrowth, which will also facilitate a uniform distribution of cells and adequate transport of nutrients and cellular waste products. For this, the minimum recommended pore size of a scaffold for bone formation is 100 μm, and a scaffold with a pore size of 200-600 μm is generally acceptable. Natural spongy bone combines good mechanical strength with high porosity, but engineering an artificial tissue that combines these properties is a challenge. In addition, any processing method needs to be rapid and inexpensive for cost-effective, large-scale operation. Several techniques have been investigated for fabricating such a porous scaffold, including solvent casting/particulate leaching, phase separation, solid freeform fabrication, polymer foam replication, microsphere sintering, and several combined methods. However, these methods cannot produce scaffolds that show both high porosity and good mechanical strength.

An article, How to fabricate porous artificial bone by injection molding July 2013 Song Zhou, Yubao Li, Li Zhang, Yanying Wang, and Shibo Gao have investigated injection molding, a rapid, convenient, and economical way to prepare a porous polymer structure. It has previously been used to fabricate microcellular polypropylene composites, including a microcellular polyamide-6 nanocomposite with pore size of 10-100 μm. The article explains the nucleation and growth of the pores are sensitive to the molding conditions and the thermo mechanical histories of the material elements. Furthermore, in many process or methods, ingredients like nano composites are used with a thermoplastic to improve the strength to compare with the existing medical PEEK. However, since the medical PEEK lacks a good compressive strength and elasticity, these characteristics are not taken under consideration when building a biomaterial for bone replacement. This invention strives to limitations of medical PEEK and understand bone to build around a better innovative biomaterial for implantable replacement.

When identifying a compressive material to blend with a thermoplastic, a natural fiber ingredient can be used for a reinforcement and or filler, however, there are many limitations in the medical market-devices and implants for this ingredient. Because the natural fiber reinforcement or filler like wood flour, kenaf, jute, hemp, sisal contain impurities, has odor and a limited processing window, it is very difficult to use in medical applications, especially, in contact with the body. Moreover, when processing these natural fibers, they degrade in the 390 F temperature range. In Joyce et al. U.S. Pat. No. 8,546,470, cellulosic fibers are used with a heat profile of polyolefin like polypropylene with a higher heat processing of a polyamide. These two polymers work synergistically with the cellulosic fiber, having a high degree of purity with a maleated polymer to provide a wider heat profile with less degradation and an increase in strength. Consequently, thermoplastic biopolymers can be considered for medical applications but need to address the element of toxicity and lack the necessary strength to replace medical PEEK, as well as, the porosity to promote cellular growth inside the molded part.

There are inorganic and organic reinforcements and fillers to increase the strength of thermoplastics, however, all must be approved by the FDA for medical devices and implants. The PEEK compositions reinforcements like carbon fiber, glass fiber for improving physical performance, has had little success with FDA approvals for Class II or Class III implants. Furthermore, thermoplastic biopolymers like PLA (poly latched acid) has had very little f any success in using reinforcements for medical applications. The natural fibers can be used with thermoplastics to increase strength in the compositions either thru adding additives or ingredients such as couplings, glass fiber reinforcements and can achieve a tensile strength of 7,000-8,000 psi. These tensile strength are very low compared to the requirements for replacement of medical PEEK implants and bone replacement.

Thermoplastic biopolymers being used in the medical market for production of medical devices and implants are being considered like PLA (poly lactide acid)which has been used for re sorbable sutures. (B. H. Brown 1998) PLLA is the polymer most commonly used for the production of bio absorbable stents. PLLA is an aliphatic polyester composed of the L-enantiomer of lactic acid (2-hydroxy propionic acid). However, this biopolymer lacks the radial strength and elasticity to replace bone in the medical market and has limited opportunity for medical devices because of the attraction and storage of water. Also, PLA degrades in the body after 6 months and then begin to be absorbed into the bodies normal metabolic systems. (Carroll 2013)PLA can also be compounded with or without thermoplastics and cannot be absorbed. At this time, these type of thermoplastic PLA materials cannot be implanted into the body and requires sufficient processing to drive out impurities. Overall, the PLA has performance, structural limitations and will be a temporary device in most of the medical applications because of the affinity to moisture. Another biodegradable material with reservable qualities like PLA is Polycaprolactone (PCL). PCL is a biodegradable polyester with a low melting point of around 60° C. and a glass transition temperature of about −60° C. The most common use of polycaprolactone is in the manufacture of speciality polyurethanes. PCL is degraded by hydrolysis of its ester linkages in physiological conditions (such as in the human body) and has therefore received a great deal of attention for use as an implantable biomaterial. In particular, it is especially interesting for the preparation of long term implantable devices, owing to its degradation which is even slower than that of polylactide. Polyanhydrides are a class of biodegradable polymers characterized by anhydride bonds that connect repeat units of the polymer backbone chain. Polyanhydrides are considered biocompatible and used for drug delivery. They are also surface eroding polymers which do not allow water to penetrate the material. Copolymerization is suggested as to exhibit bulk eroding characteristics. Bulk eroding polymers take on water like a sponge and erode inside and on the surface of the polymer.

It is known that cellulose fibers will not degrade in the body disclosed by Western University in London Ontario by Professor Wankei Wan. Furthermore, the cellulose fiber is not re sorbable by the body which is a clear differentiator compared to other natural biodegradable fillers like PLA, PLLA and PCL. There are two types of hydrogen bonds in cellulose molecules: those that form between the $C_3$ OH group and the oxygen in the pyranose ring within the same molecule and those that form between the $C_6$ OH group of one molecule and the oxygen of the glucosidic bond of another molecule. Ordinarily, the beta-1,4 glycosidic bonds themselves are not too difficult to break. However, because of these hydrogen bonds, cellulose can form very tightly packed crystallites. These crystals are sometimes so tight that neither water nor enzyme can penetrate them; only exogluconase, a subgroup of cellulase that attacks the terminal glucosidic bond, is effective in degrading it. Nam Sung Wang Cellulose Degradation There has been numerous work with cellulose fibers for implants in the body. Microbial cellulose, sometimes called bacterial cellulose is used in food and has many applications in the medical industry. The microbial cellulose is very pure, absorbs a lot of water and is grown in a production facility. Contrary, the cellulose fiber derived from trees or plants is not as purified and doesn't absorb as much water. The advantages of microbial cellulose versus cellulose produced by trees or plants include.

Finer and more intricate structure
Longer fiber length: much stronger and wider
Can be grown to virtually any shape and thickness
The formula of the media used and the strain of Acetobacter xylinum will determine the quality of the pellicle.

Microbial cellulose is biocompatible and non-toxic, making it a good candidate material for medical applications. However, the disadvantages of microbial cellulose include high price, lack of large scale production and timely expansion and maintenance of cell culture. There is on-going research to evaluate a possible role for bacterial cellulose in the following applications:

Scaffolds for tissue engineering
Synthetic dura mater
Bladder neck suspension
Soft tissue replacement
Artificial blood vessels Certain technologies with the organic compound cellulose, cellulose fibers has provided novel inventions, especially when there is a need to coat for biocompatibility in the body. By coating cellulose fiber with Plasma ionization the fibers create free carboxyl (COOH—) and hydroxyl (OH—) groups at the cell material interface. In turn, this creates a hydrophilic environment that will weaken cellular absorption, therefore increasing biocompatibility and reducing inflammation. A plasma treated cellulose material is superior in providing better compatibility, mechanical strength, and cost effectiveness. Cellulose is said to be more ubiquitous in numerous areas, making it cheaper and easier to obtain with respect to currently used polymeric implants. Plasma treatment is proven to increase biocompatibility by keeping implant cellular interface hydrophilic as opposed to currently existing solutions. However, it has been known that excessive exposure of the polymer surfaces to plasma can physically deteriorate the polymer surface over time.

Furthermore, multiple material compositions utilizing cellulose fiber could be used for construction of an implant or even a medical device. There are other forms of cellulose that have a track record of success when in contact with the body. Cellulose films have been used for wrapping purposes, it has also found an application in the treatment of renal failure, as well as, evolving clinical applications such as scaffolds in tissue engineering, temporary skin substitute, a homeostatic agent, post operative adhesion barrier and as a culture material for hepatocytes. Furthermore, cellulose has been used in the production of sutures and made into cellulose filaments. Actual carbon based sutures have been produced by the modification of cellulose filaments (Narat et al. 1950) Rayon cellulose fiber, with a plasma ionization treatment on the surface of the implant material is a new polymer base implant material. Cellulose has also been introduced in medical applications that have been used in sponges for years in operating rooms.

With strength, stiffness and elasticity being such a critical requirement for medical devices and implants, there is a big challenge to utilize natural fibers with thermoplastics for medical devices and implants. A thermoplastic biopolymer composition, when natural fibers are orientated can reach a tensile strength of 20,000 psi. There has been prior art that claims oriented fiber processes to improve strength with a particular natural fiber materials with thermoplastics. A U.S. Pat. No. 5,474,722 by Woodhams, 1998 Oriented thermoplastic and particulate matter composite material claims a continuous process used to make foamed or unfoamed composite articles have strength, modulus and density values comparable to typical hardwoods or softwoods. Furthermore, there were two types of methods used to orientate fibers, a ram extrusion type and die drawing process. Articles and demonstration occurred in 2002 at Onaga Composites utilizing the die drawn method to produce a low density oriented fiber wood composite. The U.S. Pat. No. 6,939,496 Method and Apparatus for forming composite material and composite material there from by Maine et. al 2005 describes the die drawn process and specifically claims an extrudable polymer with a cellulose based particulate filler which is a wood fibers and binders. There has also been further process and materials developed based on the die drawn method for building products that contain natural fibers, thermoplastics and silicate cement and gypsum. A Low density oriented polymer composition with inert inorganic filler U.S. Pat. No. 8,142,697 (Nichols et a. 2012) is an example of further advances of the oriented fiber method for building and construction products. Furthermore, there has been inventions that describe natural fiber with thermoplastic polymers where there are mention of orientated fibers with non orientation. Method of making cellulosic filled thermoplastic composites of an anhydride containing copolymer. ref. U.S. Pat. No. 8,221,663 Michalik et al. 2012. The above oriented fiber technologies and methods referenced include cellulosic materials that are natural fibers.i.e. wood flour, wood fibers, flax, jute, neither mention the organic compound cellulose, most preferred cellulose fibers that are made with ether or esters of cellulose, which can be obtained from the bark, wood or leaves of plants, or from a plant-based material. Furthermore, prior art utilized compositions that excluded and included an anti fungal additive that still showed mold was evident after a month of exposure to water and the elements. The mold and fungi can cause infections as it relates to this inventive art and deteriorate or cause premature failure in a product. The compositions in prior art that contained wood fiber and polyolefin with the oriented fiber method can be solved through the composition of matter in Joyce U.S. Pat. No. 7,994,241. This U.S. Patent included a polyamide, a polar polymer, in the natural fiber and polyolefin matrix, providing a resistance to fungus and mold.

It is important to identify types of natural fibers, the size of the natural fiber, as well as, the aspect ratio of the fiber because it would be very difficult to orient a fiber with very short aspect ratio. Moreover, not all natural fibers, i.e. hemp, flax, wood fiber and thermoplastic polymers will be able to orientate with the same process and have the same attributes if there is very little aspect ratio. The natural fibers in some forms is more of a filler than a reinforcement when melt blended with a thermoplastic. By processing either a natural fiber filler or reinforcement with a thermoplastic numerous times like medical PEEK, the ability to drive out toxicity will not be probable. The type of natural fiber in a thermoplastic matrix will reflect where the product could be used and for what applications. Consequently, this type of thermoplastic biopolymer material with a raw natural fiber will not be successful in medical applications. However, the processing of a natural fiber into a cellulosic fibers and or cellulose flour from a plant or tree can be applicable because of the purity. To disperse cellulose flour in a twin screw operation without agglomeration is difficult, as well as, to injection mold components and parts with consistent properties. When cellulose fibers or flour needs to be melt blended with multiple thermoplastic polymers with different melt temperatures, it becomes more of a processing challenge, in which the above processing technologies fail to discuss. The cellulose fibers or flour, being alloyed with multiple thermoplastic polymers including polypropylene and polyamide help with strength, adhesion and promoting more polarity in the composite matrix. Joyce U.S. Pat. No. 7,994,241 and Joyce et. al U.S. Pat. No. 8,546,470. The polyamide used in both U.S. Patents is significant for heat stability and adhesion, providing strength and synergy between ingredients. But also in providing a resistance to fungus and mold, something previous natural fiber material technology lacked and is necessary for the previous patented oriented fiber technology and methods in a natural fiber polyolefin matrix. Furthermore, Joyce et al. uses a combination of cellulose fiber or flour, two polymers—a hydrophilic and hydrophobic and a maleated polymer. The composition of matter has been alloyed to help promote synergy between ingredients while improving strength with lower densities. In Joyce et al. physical or chemical foaming is suggested but fails to suggest that porosity and strength can be improved with either method. Furthermore, the composition of the molded part hasn't been identified as biocompatible to provide growth for human cells and has non toxicity for ingrowth. The prior art reveals thermoplastic compositions utilizing wood fibers and a polyolefin that have impurity and are not designed or considered for medical applications.

The ability to produce ingrowth has been realized through porosity (Serafica: Gonzalo; et al 2014). Polysaccharide materials and more particularly to microbial-derived cellulose having porosity is identified suitable for cellular infiltration desirable properties for medical and surgical applications has been discussed. Consequently, this technology will allow cell infiltration while preserving the physical properties of the microbial-cellulose. As stated earlier, the bio compatibility with hydrophilic nature of a composition promotes bio compatibility. As far as structural integrity and the ability to support any load bearing is not mentioned.

The ability to foam biopolymers is evident through chemical foaming agents and physical foaming techniques. Most physical foam and chemical foam compositions lose strength. There is an injection molding process with gas assist, a physical foaming techniques that can help increase strength and flexural modulus in natural fiber compositions. Furthermore, the processing techniques utilizing high injection pressure and gas assist can strengthen parts because of the compressibility of the composition. With the right combination of gas, pressure and biopolymer composition, one can get a molded article that has a resemblance of bone. A prototype product for bone replacement that utilized gas and natural fiber composite can be identified U.S. Pat. No. 7,214,420 molded article that was produced from Robert C. Joyce.

The U.S. Pat. No. 7,214,420 Molded Article (Joyce 2007) uses wood fibers in the polyolefin matrix. The natural fiber polyolefin composition has been injected into the tool at high pressure and is compressed by gas injection to achieve an impervious skin with high strength. This 3 dimensional molded article with glass fiber reinforcement can achieve tensile strengths of 7,000 to 8,000 psi and with the pressurized cavity can be increased but will fall short of the desired 15,000-20,000 psi requirements for a replacement of medical PEEK. Furthermore, the wood fibers in the polyolefin composite have impurities that promote lubricity and degradation at processing temperatures of polyolefin's –400 F. The wood fibers in the polyolefin matrix have an elongation of 2 to 3% which is brittle and not very elastic.

BRIEF SUMMARY OF THE PRESENT INVENTION

This invention is a longitudinal body having oriented fibers that will comprise of an organic compound, most preferably, cellulose fiber, a hydrophilic and hydrophobic polymer. The composition will have absorbable and non re sorbable qualities in the body with an internal construction for cell and tissue in growth. This invention has a high degree of purity, showing non toxicity in a basic viability cell test. There is high compressive strengths for a thermoplastic plastic composition with performance improvement, to include a lower specific gravity better elongation, and tensile strengths.

The advanced material composition containing cellulose fiber is processed with two thermoplastics, specifically, a polar polymer, most preferred polyamide, a PET (Polyethylene terephthalate) and non polar polyolefin, preferably a polypropylene, either a high crystalline, co polymer or homo polymer, into a pellet form. It is preferred to use a coupling that bonds the neutrality of the one non polar polymer to the other polarized ingredients. Furthermore, based on the injection molding and testing of the composition by standard ISO or ASTM methods, there is an improvement in properties over previous art that included wood fiber thermoplastic compositions, see Table 1. In combination of cellulose fiber at minimal loadings, most desirable at 20% but can be preferred at either 10 to 40% cellulose fiber, possibly a coupling agent, with other specified thermoplastics such as polyamides and polypropylene, one can promote improved dispersion and consistency of the composition, better adhesion and strength of the matrix.

These ingredients listed above have been exposed to the body in one form or another. The cellulose fiber is a hydrophilic material that has a surface charge and inner charge that affect the bonding strength of the fiber thermoplastic network. The fiber charge is a significant characteristic of cellulose fibers, which strongly affects the post processing of cellulose fibers, such as enzymatic modification, and the properties of cellulose based end products. The cellulose fiber charge unlike wood fiber, is highly revenant to fiber hydrophilicity and swelling ability. The polyamides are also hydrophilic and of a polar nature with excellent radiation resistance and have shown to support cell culturing. The polypropylene, a non polar polymer and when exposed to the body, has been identified as non toxic with fair radiation resistance. The combination of ingredients above present a powerful solution for medical devices and implants that include a hydrophobic environment at the cell-material interface.

By orientation of the cellulose fiber thermoplastic composition there is further improvements in properties versus other natural fiber thermoplastic compositions such as cellulose based wood flour. The orientation of the cellulose fibers will further reduce the weight of the molded part and help improve the cell and tissue adhesion in the composition. It is suggested that the composition be pulled through a die, similar to the die drawn method, versus a ram extrusion where the composition is pushed through a die and pulled by a belt or motor driven puller. In previous art, the draw down method will produce higher tensile tensile and did not consider the compression strength for axial loads or torques required to in medical devices or some implants. The longitudinal body in the invention will utilize a more sophisticated die drawn method for processing and utilize FDA compliant ingredients including the natural fiber i.e. cellulose fibers. For the required loads the thermoplastic cellulose composition will have improved elasticity with improved tensile strength and a higher degree of compressive strength after processing.

The die drawn process method to orientate the fibers will have a high drawn down ratio but since the thermoplastic cellulose fiber composition will react more like an amorphous resin, differently than the compositions with cellulose based materials, most preferably a 12-25%. Also, the longitudinal body can be constructed with a smooth skin or texture unlike the previous method. Furthermore, the improved performance characteristics will be supported through various die advancements in cooling and heat transfer that will also will help generate better strength, elasticity and more controlled and repeatable small porous structure. Once the longitudinal body is cut, to the naked eye, you will not see a porous structure. Furthermore, once this longitudinal body is cut, a lateral body can be formed by machining and or compression molded to achieve a three dimensional part. This three dimensional part can be processed to improve surface energy with various porosity dimensions to replicate bone implants and or a medical device.

To produce an extruded filament for 3 D printing, approximately 1.75 mm to 3 mm in diameter with the cellulose thermoplastic alloy composition, it is preferred to have some if not a large portion of the cellulose fibers orientated while 3 D printing. The filament with oriented cellulose fibers in the thermoplastic matrix will have an improved tolerance and dimensional stability. Many 3 D printing customers often underestimate the importance of dimensional control of the filament. Because the cellulose fiber is compressible and hygroscopic, prior art cannot produce the necessary filament with consistent quality and speed necessary for production without modification. Furthermore, the technique to improve strengths and stiffness is to compress the cellulose fiber in the composition through increasing the Ian length and pitch in the die. Unfortunately, this technique helps to increase the density which the inventor has been suggesting, which is to promote better strength, and elongation with porosity versus non oriented fiber. To make this oriented fiber filament, the cellulose fibers in this composition is not modified but will have new equipment for process control for maintaining a low density and keeping size reduction with improved accuracy within dimensional control.

A filament for 3 D printing could be extruded containing a thermoplastic polyolefin with >20% cellulose fiber by volume at 1.55 mm diameter. The cellulose thermoplastic composition with more >20% cellulose fiber was 3 D printed printed without fiber orientation. The filament containing a oriented cellulose fiber in a thermoplastic containing polyolefin and a polar thermoplastic is contemplated by the inventor to achieve stronger properties more than 4 times that of non oriented fibers in a filament for a 3 D Printed part. The cellulose fiber is relatively small <120 micron with a 6 to 1 aspect ratio to be printed with consistent patterns and shapes. It has also been observed by the inventor that indeed the composition in a 3 D printed part will have a reduction in specific gravity, much less than the specific gravity of the standard testing methods ISO or ASTM. A thermoplastic composition containing two different crystalline structures that included polypropylene, polyamide and cellulose fiber in a non oriented form being 3 D Printed part produce good strength with lightweight construction, little if any warp, unlike traditional parts made with polypropylene. It is also contemplated that due to the increase in elongation in using cellulose fibers with thermoplastics as described in Table 1. to actually wind the thermoplastic cellulose fiber around the spool would have less of a chance to break and stretch much better than other forms of natural fiber. i.e. wood fiber. It is contemplated by the inventor that not all filaments needed to be 3 D printed are wound around a spool but could be made into sticks of very small diameter 1.36 mm to 1.75 mm with lengths anywhere between 250 mm to 340 mm. Furthermore, in keeping the orientation of the fiber, the printer could accommodate various angles for applying the filament in keeping the fibers aligned in the thermoplastic matrix.

As stated previously, the present invention will utilize an organic compound cellulose, most preferred a cellulose fiber having the ability to absorb but not be resorbed by the body with the two thermoplastic polymers providing hydrophilic and hydrophobic characteristics. The orientation method will provide improved performance with the cellulose fibers and the two thermoplastic polymers. The present invention with a compressible nature in the cellulose fiber can create new and inventive medical products that require more elasticity and torque related movements for various implants like spinal cages. It is further contemplated that one can include production of improved orthotic devices and sports equipment, such as helmets, lightweight pads and body armor.

The ingredients in this invention are critical to the performance of the molded parts to produce medical products including devices and implants such as spinal cages. The hydrophilic nature of the cellulose fiber provides necessary compressibility for some implants that require certain degrees of torsion or axial movement. Furthermore, cellulose fiber and the derivatives are well tolerated by most tissues and cells. These non-toxic materials have good biocompatibility, therefore, they offer several possibilities in medical applications. Matter of fact, regenerated cellulose sponges have been used in experimental surgery for decades and it does not effect the healing process, but acts as a chemoattractant producing cells involved in the repair process to migrate towards it. Furthermore, the polyamide attracts moisture but can also help provide cell adhesion. The polyamide can synergistically interface with the cellulose fibers, and the other ingredients like the polypropylene. Through high sheer and temperatures in the 470 to 490 F in an extrusion process the polyamide will alloy with the polypropylene. In the injection molding process, it has been observed where the combination of the two different polymers melt between 370 to 400 F. The polypropylene which is hydrophobic and will repel the water molecules forming ionic or a hydrogen bond with the water molecule. Hydrophobic interaction plays the most critical roles in the formation of the lipid bilayer of the cell membrane and the folding of proteins and nucleic acids. However, when the cellulose flour is melt blended with multiple thermoplastics like polypropylene and polyamide in a composition to include a reinforcement like glass fiber, the composition does not have the necessary strength to replace a medical PEEK for medical applications.

The secondary operations are needed to promote improved physical properties, as well as, have unique coating and or adhesion properties like PEEK that is desired in the medical products market. Furthermore, this invention will have a porous structure, that is almost half the specific gravity as PEEK, promoting a much improved strength to weight ratio, which can help in improving a patients energy level. The skill to create a thermoplastic cellulose biopolymer with oriented fibers to replace a high strength PEEK implant for medical products, devices, implants, instruments, was neither conceived or identified in previous art.

There has been a desire to utilize thermoplastics because of the flexibility in forming and customization of the material. To overcome the deficiencies in a molded part for medical devices and implants, the present invention is a molded part that utilizes a thermoplastic cellulose biopolymer composition in a preferred compounded pellet form. This pellet will be extruded into a billet form and furthermore oriented by the process to improved the physical properties required in the applications. It is also possible to have the identified ingredients, no less than cellulose fibers, polyolefin and polyamide fed directly into an inline extrusion system process that will orientate the cellulose fiber to produce a molded part with significant strength and elasticity.

However, by itself, this organic compound with thermoplastics that is identified cannot replace a molded part made from PEEK unless there is a process method to help orient the cellulose fibers. The process to orient the cellulose fibers with the two polymers no less can include an in line process where all ingredients are processed at once or where certain ingredients are combined and then fed into the extruder for cellulose fiber orientation. It is contemplated by the inventor that since certain extrusions, such as a filament for 3 D printing will require very tight tolerance, a compression mechanism attached or integrated to the inline puller will be required downstream.

Prior art fails to discuss biopolymer compositions with oriented fibers, specifically cellulose fibers and two specific thermoplastic resins—polyolefin and polyamide, having two different melt temperatures. The SEM micrographs in the brief description of several views of an oriented fiber made of wood fiber and polyolefin show a highly porous structure with Interconnecting pores which is similar to bone. The oriented fiber compositions in combination of ingredients that include no less than cellulose, polyolefin and polyamide can further provide the additional strength and elasticity necessary to overcome the existing challenges mentioned in prior art. In addition, the invention contains polyamide which will not prohibit human cell growth and cellulose fibers, an absorbable material, providing better strength and elongation versus natural fibers like wood, jute, kenaf. Furthermore, the longitudinal body will have ingredients that blend with a hydrophobic polyolefin to maintaining a low specific gravity and promote biocompatibility. Most importantly, the medical industry requires a high level of purity in all materials that are implanted into the body. The invention describes ingredients that have been introduced to the body in some form without adverse affects unlike some polymer compositions that need to be extensively processed for purification, not biocompatible or re sorbable. The molded part having a degree of porosity that can expose the cellulose fibers and one or more hydrophilic polymer. This exposure will help with the necessary biocompatibility for the medical applications such as implants.

The hydrophilic nature of the cellulose fiber is important for tissue to adhere to the composition. It has been identified that there is multiple forms of cellulose which can be chemically separated from lignin and hemicellulose, as well as, microbial cellulose grown in the laboratory.

Cellulose is also odorless and has no taste. It is further realized that cellulose doesn't continue to soak of liquids and store them like other bio fillers such as starch, PLA, PHB. Furthermore, it is realized that cellulose doesn't degrade in the body, which is important as a medical implant. Moreover, cellulose is a purified organic compound with very good heat resistance and can process well in a thermoplastic without clumping and dispersion issues.

It is preferred that the molded part will have some degree of porosity to help create better structure and strength for desired medical applications, more specifically, medical devices and implants for the body. The porosity will help promote cell growth inside the two or three dimensional molded part. Furthermore, this high strength biopolymer part with two dimensional features will be an innovative core or end product with a superior strength to weight ratio. The combination of ingredients and fiber orientation will attract in vitro cell growth which has been illusive for medical devices, implants. This biopolymer composition has a composition comprising of no less than cellulose fiber, polyamide and PP with orientated fibers. It is further anticipated that nano cellulose added to the thermoplastic cellulose biopolymer composition will enhance the strength of the biopolymer cellulose composition with oriented fibers.

The composition will perform like PEEK, a high strength material after processing to orientate fibers. This composition will have a lower specific gravity and be at a lower cost. It is expected that the thermoplastic cellulose composition with orientated fiber will have tensile strengths greater than 14,000 psi.

Though PEEK can be compression molded, the high temperature processing requirements might limit the applications. Thermoplastic biopolymer compositions can also be compression molded. In some molding techniques for thermoplastic compositions fibers can be driven from the surface by heat and pressure. Below is three categories for existing technologies to improve strength in biopolymers:

a. To alloy a thermoplastic or melt blend one thermoplastic with another polymer having more strength and heat resistant with natural fiber.
b. To process with gas in order to compress fibers against the wall structure of the part.
c. Orientation of fibers in a thermoplastic matrix.

To achieve the mechanical property replacement for bone and create implantable devices for the medical industry there needs to be a combination of thermoplastic cellulose material and process to achieve the desired molded part. Standard methods to produce test bars, i.e. ASTM or ISO methods, for material qualification to compare against other resins, isn't practical for applying cellulose fiber thermoplastic compositions, mainly because of the compressibility of the composition. Furthermore, the thermoplastic cellulose fiber alloy composition identified in the present invention has not been suggested by other methods or processed in a manner with two extremely different melt temperatures to achieve the necessary performance requirements for the applications mentioned. It is most necessary to combine the ingredients in the composition which contain a cellulosic fiber, a hydrophilic and hydrophobic polymer to deter not only mold and fungus growth but show biocompatibility to achieve the necessary requirements to make the molded part for the medical applications like devices and implants. Also, the inventor has contemplated two if not three process's to complete the task of molding a very strong and porous part. These various process's can include extrusion, compression molding, laminating, machining or milling. Furthermore, it is preferred that the compression molding process, with various heats and pressures profiles can close the pores of the bar, sheet or rod stock. More specifically, with bar stock made from the invention, one third of the part can be machined with a CNC lathe and then compression molded so that density at the surface will reflect less friction and or restriction when another surface will touch i.e..bone socket.

Other processing techniques to help create three dimensional parts would include over molding which is commonly referred to as insert molding. The two dimensional shape can also be reheated and compression molding to form a three dimensional shape. The inventor had chosen to utilize compression molding of biopolymers in a secondary process will help drive out the porosity in a part at the surface to help with the wear of medical device or implant.

Furthermore, the two dimensional form can be a rectangle size of 9 mm×26 mm, or 30 mm round or a square stock that is 50 mm. These two dimensional forms, the bar and or rod, in this case, would be cut to length in a secondary process to be machined or injection molded for a three dimensional finished part. Also process techniques like additive manufacturing or 3 D printing has been used to create medical implants and bone replacements. The compositions used in 3 D printing have been primarily an ABS or PLA for medical devices and implants but have not been too successful with structural performance and compatibility with the body. Additive manufacturing with thermoplastic biopolymers utilizing glass fiber reinforcements and or mineral fillers have had limitations and restrictions. These limitations for reinforcements and fillers in thermoplastic compositions include dispersion of fibers and flow. These reinforcements can also be very abrasive and cause considerable wear in the tooling.

DETAILED DESCRIPTION OF INVENTION

The longitudinal body will be constructed from a composition comprising of at least two polymers, preferably a polyolefin and polyamide with an organic compound, most preferably cellulose fibers. Through a high shearing process while being melt blended, the alloying of both polymers is performed, then downstream the organic compound is dispersed to obtain a non orientated fiber composition. The cellulosic fibers and the two polymers with different melt temperatures will then be pulled through a die to orientate the composition producing a longitudinal body with higher strength and improved elasticity. The longitudinal body will also have a high degree of compressive strength and porosity for tissue or cell ingrowth that is necessary for an implantable bone or device to be more stable in the body. Once the longitudinal body been cooled and cut, a CNC machine process can cut or mill to produce a finished part. There may be a requirement to thermoform or compression mold or even apply a coating to the molded part in a third operation with or without the same composition. The invention will produce a more sophisticated longitudinal body with the ability to achieve a lateral dimension through a secondary process.

The cellulose fibers in the present invention are derived from natural fibers i.e. trees and plants with a micron size of 80-100. The wood fibers are much larger, in the 120-140 micron size. Furthermore, there is considerable differences in using a wood fiber, an impure fiber in the composition below versus utilizing an organic compound, most preferably cellulose fibers, that can be classified or manufactured. This cellulose fiber is a much purer fiber, lacking the lignin, hemicellulose in the thermoplastic biopolymer composition. See Table 1 below. It is evident that the testing provided distinct mechanical differences. Some distinct differences also included compressibility of the cellulose fibers, as well as, strength which can relate to the improved elongation/adhesion in the thermoplastic matrix. Furthermore, the compressibility and or torque movement is important in implants like spinal cages.

It has been observed by the inventor that by providing an extreme amount of injection pressure in an injection molding process, more than 14,000 psi can increase the specific gravity by 30% compared to no injection pressure. Furthermore, it is believed the compressive strength, compressibility of the cellulose fibers in the composition are of great value in torque related movements in certain implants. This invention utilizes an orientation method to orientate the cellulose fiber with two different polymers, preferably a polyamide and polyolefin, having different melt temperatures, at a very low specific gravity, less than 75 g/cc and increase the tensile strength by 250% of the polyolefin. Furthermore, the inventor concludes the longitudinal body will be compressible, have porosity with a tensile strength beyond 14,000 psi. The compressibility of the longitudinal and lateral body is most desired in moment of force or torque. Furthermore, using the standard ASTM test methods of the thermoplastic composition comprising of polyolefin, polyamide with >20% cellulose fibers in a injection molding process with injection pressure at 16,000 psi, there is a specific gravity at 1.01 g/cc. A 20 to 30% higher specific gravity than observed with the same composition with no injection pressure, i.e. 3 D printed. The thermoplastic cellulosic fiber alloy composition with >20% cellulose flour has a 0.60 g/cc specific gravity when 3 D printed.

The thermoplastic cellulose fiber alloy composition was made in a pellet form and injection molded into plaques contained less than the preferred 25% of cellulosic fibers, with no less than 20% cellulose fiber having 95% FDA compliant ingredients. This biopolymer composition included cellulose fiber, polyolefin, coupling and polyamide. The injection molded plaques were immersed in the culture medium for 16 hours and tested for Basic cell toxicity requirements. The human embryonic kidney cells were seeded on the material. After 24 hours, the biopolymer material was transferred to an another well. MTT assays were performed to measure cell viability. The initial studies showed that the biopolymer material is non-toxic and human cells grow in it's presence. It is further suggested that this biopolymer material containing no less than a cellulose fiber, polyolefin and polyamide could be a replacement for medical PEEK in some applications.

The thermoplastic cellulose composition in Table 1 consists of two or more polymers with different polarity and melt temperatures being fed into the extruder with natural fibers preferably cellulose fiber in a flour or powder form. More specifically, two polymers will consist of at least one polar polymer, preferably polyamide and or PET while the other polymer is a polyolefin which has no polarity. The polar polymer will most likely be hydrophilic, requiring moisture to be removed from the composition during extrusion.

TABLE 1

Natural Fiber Property comparison

| Test | Method | Wood flour/PP | Wood/ Cellulose/ PP 60/40 | Cellulose/ PP 60/40 |
|---|---|---|---|---|
| Filler content | | 30% wood flour | 15% cellulose 15% wood flour | 30% cellulose |
| Melt Index | ASTM D1238 | 12.4 | 10.2 | 16.7 |
| Specific Gravity | ASTM D792 | 1.01 | 0.99 | 0.99 |
| Tensile Strength | ASTM D638 | 19.52 (2828 psi) | 26 (3,800 psi) | 27 (4,025) |
| Elongation @ yield | ASTM D638 | 2.1 | 5.3 | 6.3 |
| Flexural Modulus | ASTM D790 | 2820 (409,000 psi) | 2760 (405,000 psi) | 2818 (400,700 psi) |

Important observations in the property comparison that include the cellulose fibers and wood fibers with polypropylene and polyamide are shown in Table 1. The melt index, tensile strength, flex modulus and elongation show improvement with the cellulose fibers even though the fibers are much smaller. It is recognized in the present invention that the smaller cellulose fibers can further improve strength and elongation properties in the polyolefin matrix and are a better reinforcement than larger wood fiber particles. Also, the cellulose fibers lack the impurities like wood fiber, promoting better adhesion in the thermoplastic matrix. These differences in cellulose fiber construction, meaning size, purity, adhesion and length along with two polymers with different melt temperatures—polyamide, polypropylene will greatly effect the end result of a molded article. The preferred cellulose fiber in the invention has an aspect ratio of 5-1 to 8-1 but could be in a range from 3-1 to 4-1. The cellulose fiber used in the present invention is a particle size of 120 to 80 with a 4-1 and 6-1 aspect ratio. However, the micron size can be 80 to 60 but can be of a microcrystalline particle size.

A perspective view of the longitudinal body cross section, having a thermoplastic cellulose fiber alloy composition with oriented fiber, will have porosity throughout the composition of the body and a polymer rich surface on the skin of the molded part. The porosity in the molded article can be created through a pulling or stretching of the cellulosic fiber composition with or without physical or chemical foaming. It is necessary for the process to include constant melt pressure, preferably controlled by a melt pump, with a die to draw down a solid or semi solid thermoplastic cellulose fiber alloy composition to help orientate fibers. The preferred die configuration will requires heating the solid non oriented fiber composition and cooling through a rapid heat cool mechanism. The mechanism will assist in orientation of the solid or semi solid thermoplastic cellulose fiber alloy composition to provide the necessary quality and performance attributes to replace other high strength materials, i.e. PEEK and existing oriented fiber cellulose based wood fiber methods. Furthermore, the orientation method with the composition will be able to align the cellulose fibers to greatly improve tensile strength of the polypropylene by a minimum of 100% and improved compressive strength and elasticity.

The inventive longitudinal body will have porosity and promote a "no break" scenario providing solutions for applications that require significant loads with superior elasticity.

The thermoplastics cellulose biopolymer composition has a water absorption rate at less than 0.21% in a 24 hr. soak, with two hydrophilic ingredients, approximately 20 to 25% cellulose fiber and 11% undried polyamide. However, able to carry moisture into to process creating porosity into the two dimensional part, a drying procedure can remove moisture before processing. Moisture can also be removed during processing through a vacuum and or atmospheric vent. For the most part, porosity can be created through a combination of the composition and process and can be maximized or minimized. It is most preferred that there is some porosity in the molded article to promote cell or tissue growth into the part for creating additional support for the molded part in the body.

Based on the requirement of the thermoplastic cellulose fiber composition, it is preferred to have two extruders, however; one extruder can process the polymer composition so that melt blending can produce a homogenous mix. The compounding extruder that produces the compound having ingredients, i.e. cellulose fibers, polyamide and polypropylene is preferably a twin screw extruder either a 38 to 1 or 40 to 1 L/D. The cellulose fiber is fed into the mid section of the barrel and screw, heated and processed with the polymers and or additives. Furthermore, if the thermoplastic cellulose fiber composition is processed by one extruder, the machine will have multiple atmospheric vents, with a vacuum to drive out any volatiles and moisture. Since the polar polymer has a higher melt temperature, it Is preferred to be fed at the throat of the machine with high shear and temperatures at 460 to 480 F. Further down the barrel of the extruder, the cellulose fiber will be fed into the thermoplastics and dispersed into the melt blend.

In some cases, cellulose fiber is best exposed to an initial heat history of 400 F by a secondary extruder or auger system, to remove moisture at minimum 3 to 5%. Then by means of a crammer type feeder the cellulose fibers are fed into the extruder to be processed with the polymers. Once the all the ingredients are compounded in the extruder, there is a pellet die that produces various size pellets from micro pellets to pellets the size of 0.230. These pellets that are produced will have non oriented fibers. The twin screw compounder that produces these pellets has a screw design with high shear elements at the throat and very low shear where the cellulose fibers are fed into the side of the barrel. The operator controls the temperature zones in either a reverse profile –480 F at the throat or zone 1 and 380-400 F near breaker plate. Or, a bell shaped profile, which are include zone 1 at 475 F, 480 F in zone 2, 490 F, in zone 3, 460 F zone 4, 420 F zone 5, 410 F, zone 6, 400 F, zone 7 390 F and zone 8 390 F.

It is critical to utilize the operators reverse or bell shaped profile to alloy the two different polymers and make the thermoplastic cellulose fiber alloy composition. Furthermore, the orientation method utilizing a die drawing process of the cellulose fibers is required to make the longitudinal body. A continuation process or in line compounding process can produce a profile or multiple strands that would be die drawn.

The die drawing of the thermoplastic cellulose fiber alloy composition is preferred to be in a solid but can be in a semi solid state profile.

Another aspect of creating a longitudinal body having oriented fiber from a thermoplastic cellulose fiber alloy composition can be through a secondary process that uses a pelletizing process, i.e. water ring pellet, strand pellet or underwater pellet. These pellets having non orientated thermoplastic cellulose fiber are fed into an extruder. In the preferred process, a single screw extruder would melt the pelletized thermoplastic cellulose fiber alloy composition at a 370-400F, far below the melt temperature of the polyamide. This pelletized thermoplastic cellulose fiber alloy composition would be extruded with other additives if necessary, like a color concentrate and fed into a profile die at the end of the extruder. This extruded profile being in a semi or solid state form has the cellulose fiber oriented through a die with at least a 10:1 LAN length ratio and a polymer drawdown at 15-20%. This die drawing of the thermoplastic cellulose fiber alloy composition can be independent of the extruder or through a die attached to the extruder. If the die drawing of the composition is performed independently, mostly preferred, a rapid heat and cool method utilizing a heat induction mechanism is desired. The heat cool induction mechanism will be able to bring the solid state profile to desired melt quickly and cool the profile for a desired smooth skin surface. Furthermore, this longitudinal body will have an improved porous and elongated structure with a smooth like skin versus prior art. This longitudinal body will then be cut into a longitudinal body for a 3 D filament, profile, rod or sheet.

A sample filament was created in a non oriented cellulose fiber thermoplastic composition for 3 D printing. The filament was processed at 195 C with the ability to wind on a 1 kg spool. Furthermore, the inventor believes that an oriented cellulose fiber and a thermoplastic composition having porosity can be a filament for a 3 D printing process. The invention can also utilize oriented fiber in 3 D printing operation, in a wound filament form or a rod shape to be utilized by various 3 D printers.

The machining of the cellulose thermoplastic composition in an oriented fiber part will have exposed pores for cell or tissue in growth in most cases, however, some molded parts will require a combination of non porous and porous surfaces. The surface porosity of the oriented molded part can be closed through heat and pressure. It is most desired that some surfaces have a certain difference in energy levels for various applications. This compression molding operation/approach will help compress the fibers bringing polymer to surface while gaining in strength and surface hardness as well as promoting a smoother surface to have less friction. This process can be completed by compression molding operation in certain areas of not all areas of the oriented fiber rod, bar or sheet stock.

It will be appreciated the instant invention is a longitudinally extending body that is made with an organic compound having orientation of the cellulose fibers. There is at least one wall that not only has oriented cellulose fiber with porosity, having a compressive strength and elasticity for improved torque and axial load requirements better than human bone. The exterior surface is smooth to the touch and can be further processed with a CNC lathe and or machine center to form a longitudinal and lateral body. It is preferred that the longitudinal body be produced by a oriented method, preferably a die drawn method with a blowing agent, to orientate the cellulose fibers in the thermoplastic alloy composition. The thermoplastic organic fiber composite mix comprising at least ten percent by weight of cellulose fiber, preferably at least twenty percent and, even more preferably, thirty or more percent by weight of cellulose fiber. In a preferred embodiment, the hydrophobic polymer is a polyolefin. The hydrophilic polymer is a polyamide and or PET.

In another preferred embodiment, the body contains a pigment so that it can be produced by oriented fiber method. In still another preferred embodiment, the article contains a sufficient amount of a white pigment that its color simulates that of natural bone.

The invention claimed is:

1. A printed 3 dimensional article that is non-resorbable in a body and has a cellular structure, comprising:
   cellulose fibers lacking lignin and hemicellulose, and having moisture removed at a minimum of 5%,
   wherein the printed 3 dimensional article has a specific gravity below 1.0 with surface porosity,
   wherein the printed 3 dimensional article is produced by 3D printing of a composition comprising a melt blended polyamide and polyolefin with oriented cellulose fibers having chain lengths between 300 and 1700 units,
   wherein the printed 3 dimensional article has cellulose fiber alignment,
   wherein the surface porosity comprises printed pores that are interconnecting,
   wherein the cellulose fibers have an aspect ratio ranging from 3:1 to 8:1 and wherein the printed 3 dimensional article has a combination of porous and non-porous surfaces of the composition.

2. The printed 3 dimensional article of claim 1, wherein the cellulose fibers comprise pectin.

3. The printed 3 dimensional article of claim 1, wherein the composition comprises a coupling.

4. The printed 3 dimensional article of claim 1, wherein the composition further comprises a pigment.

5. The printed 3 dimensional article of claim 1, wherein the printed 3 dimensional article is produced without physical or chemical foaming.

6. The printed 3 dimensional article of claim 1, wherein the cellulose fibers make up at least 10% by weight of the printed 3 dimensional article.

7. The printed 3 dimensional article of claim 1, wherein the cellulose fibers make up at least 20% by weight of the printed 3 dimensional article.

8. The printed 3 dimensional article of claim 1, wherein the cellulose fibers make up at least 30% by weight of the printed 3 dimensional article.

9. The printed 3 dimensional article of claim 1, wherein the polyolefin comprises polypropylene.

10. The printed 3 dimensional article of claim 1, wherein the printed 3 dimensional article comprises a coating applied thereon.

11. The printed 3 dimensional article of claim 1, wherein the cellulose fibers are derived from trees or plants.

12. The printed 3 dimensional article of claim 1, wherein the cellulose fibers are exposed.

13. A printed 3 dimensional article that is non-resorbable in a body and has a cellular structure, comprising:
    cellulose fibers lacking lignin and hemicellulose, and having moisture removed at a minimum of 5%;
    wherein the printed 3 dimensional article has internal porosity;
    wherein the printed 3 dimensional article has a specific gravity below 1.0;
    wherein the printed 3 dimensional article is produced by 3D printing of a composition comprising a melt blended polyamide and polyolefin with oriented cellulose fibers having chain lengths between 300 and 1700 units;
    wherein the printed 3 dimensional article has a combination of porous and non-porous surfaces of the composition;
    wherein the printed 3 dimensional article has cellulose fiber alignment;
    wherein the cellulose fibers have an aspect ratio ranging from 3:1 to 8:1 and wherein the printed 3 dimensional article comprises printed pores.

14. The printed 3 dimensional article of claim 13, wherein the printed 3 dimensional article comprises a coating applied thereon.

15. The printed 3 dimensional article of claim 13, wherein the cellulose fibers are exposed.

* * * * *